United States Patent [19]

Fayter, Jr. et al.

[11] Patent Number: 4,522,749
[45] Date of Patent: Jun. 11, 1985

[54] PROCESS FOR AUGMENTING OR ENHANCING THE AROMA OF A FRAGRANCE BY ADDING A VINYLCYCLOPROPANE COMPOUND

[75] Inventors: Richard G. Fayter, Jr., Fairfield; Eugene G. Harris, West Chester, both of Ohio

[73] Assignee: National Distillers and Chemical Corporation, New York, N.Y.

[21] Appl. No.: 547,159

[22] Filed: Oct. 31, 1983

Related U.S. Application Data

[62] Division of Ser. No. 333,212, Dec. 21, 1981.

[51] Int. Cl.$^3$ .......................... A61K 7/46; C11B 9/00
[52] U.S. Cl. ................................ 252/522 R; 560/124
[58] Field of Search ..................................... 252/522 R

[56] References Cited

U.S. PATENT DOCUMENTS 4,431,576  2/1984  Martel et al. ................... 252/522 R Primary Examiner—Anton H. Sutto
Attorney, Agent, or Firm—Kenneth D. Tremain; Gerald A. Baracka

[57] ABSTRACT

Novel 2-vinyl-1-ketocyclopropane-1-carboxylates and 2-ethyl-1-ketocyclopropane-1-carboxylates useful as fragrance chemicals, pesticides, herbicides and chemical intermediates are provided. The invention also relates to a process for augmenting or enhancing the fragrance qualities of a formulation by the addition thereto of certain 2-vinyl-1-ketocyclopropane-1-carboxylates.

4 Claims, No Drawings

PROCESS FOR AUGMENTING OR ENHANCING THE AROMA OF A FRAGRANCE BY ADDING A VINYLCYCLOPROPANE COMPOUND

This application is a division of application Ser. No. 333,212, filed Dec. 21, 1981.

BACKGROUND OF THE INVENTION

1. Field of the Invention

The present invention is directed to novel cyclopropane compounds and, more specifically, to 2-vinyl and 2-ethylcyclopropane compounds having a single carboxylate moiety present on the ring. The compounds of this invention are useful as chemical intermediates, pesticides, insecticides and as fragrance chemicals.

2. Discussion of the Prior Art

Pyrethrin and various synthetic compounds modeled thereafter, such as allethrin, are well known and while primarily recognized for their insecticidal properties are also useful for a variety of other applications. In view of the diverse physical and chemical properties possible with such products, much effort has been directed to the synthesis of other structurally related compounds, i.e., based on the cyclopropane structure.

Various cyclopropane monocarboxylate compounds have been prepared, however, most of these reported compounds have substituents other than hydrogen at the three ring positions. For example, in U.S. Pat. No. 4,180,446 dihalogen vinylcyclopropanecarboxylic acid esters of the formula

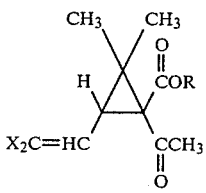

where R is an alkyl moiety and X is chlorine or bromine are obtained by a photochemical ring contraction of a correspondingly substituted dihydrofuran compound. Cyclopropane compounds useful as pesticides or pesticide intermediates and having the formula

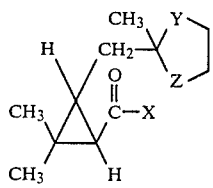

wherein Y and Z each independently is oxygen or sulfur and X is chlorine, bromine or OR in which R is hydrogen, a salt-forming cation, an alkyl group or residues of certain other alcohols have also been disclosed in U.S. Pat. No. 4,225,612.

Cyclopropane monocarboxylate compounds having only two of the ring positions substituted have been reported by Kierstead et al. (J. Chem. Soc., 1953, 1799–1803). Kierstead et al. prepared ethyl 1-acetyl-2-vinylcyclopropane-1-carboxylate by the condensation of ethyl sodioacetoacetate with 1,4-dibromobutene-2. The ability to obtain other related compounds was restricted, however, due to the limitations of the condensation reaction employed by Kierstead et al.

SUMMARY OF THE INVENTION

Novel cyclopropane monocarboxylate compounds useful as pesticides, herbicides, fragrances and chemical intermediates and having an acyl and carboxylate group substituted on the 1-position of the ring and a vinyl or ethyl group in the 2-position of the ring have been prepared. The cyclopropane monocarboxylates of this invention correspond to the general formula

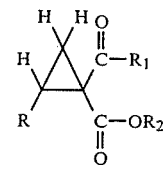

where R is an ethyl or vinyl group, $R_1$ is an aliphatic or aromatic group and $R_2$ is an aliphatic, cycloaliphatic or aromatic radical. When $R_1$ is an aliphatic group, it will typically contain from 3 to 12 carbon atoms and when $R_1$ is aromatic, the group will contain from 6 to 18 carbon atoms. $R_2$ can contain from 1 to 30 carbon atoms and can be an aliphatic, cycloaliphatic or aromatic hydrocarbon radical or an aliphatic, cycloaliphatic or aromatic radical containing one or more oxygen, sulfur, nitrogen or halogen atoms.

Especially useful 2-vinyl-1-ketocyclopropane-1-carboxylates of this invention having utility as fragrance chemicals and intermediates and which can also be employed as chemical intermediates in the preparation of more complex molecules are compounds of the above formula wherein $R_1$ is an alkyl or alkenyl group having from 4 to 8 carbon atoms, phenyl, benzyl or $C_{1-4}$ alkyl- or $C_{1-4}$ alkoxy-substituted phenyl or benzyl and $R_2$ is a $C_{1-4}$ alkyl group.

DETAILED DESCRIPTION

The novel cyclopropane monocarboxylate compounds of this invention correspond to the general formula

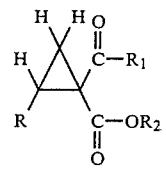

where R is an ethyl or vinyl group, $R_1$ is an aliphatic group having from 3 to 12 carbon atoms or an aromatic group having from 6 to 18 carbon atoms, and $R_2$ is an aliphatic, cycloaliphatic or aromatic hydrocarbon radical or aliphatic, cycloaliphatic or aromatic moiety containing one or more oxygen, sulfur, nitrogen or halogen atoms. Various geometric and stereo isomers of the cyclopropane monocarboxylate compounds, and mixtures and racemates thereof, can exist. For example, by varying the process and reaction conditions by which the compounds are prepared it is possible to impart preferential optical activity. Whereas the formula does not take into account isomeric forms, i.e. cis- and trans-configurations and dextro and levo forms, it is intended that the invention be construed to encompass all such forms and mixtures thereof.

The radical $R_1$, when it is aliphatic, can be either straight-chain or branched-chain and can be saturated or contain one or more sites of unsaturation. Alkyl and alkenyl groups having from 4 to 8 carbon atoms are particularly advantageous. When $R_1$ is aromatic, one or more alkyl or alkoxy groups having from 1 to 8 and, more preferably, 1 to 4 carbon atoms can be present on the ring. Phenyl, benzyl and $C_{1-4}$ alkyl- or $C_{1-4}$ alkoxyl-substituted phenyl or benzyl radicals are preferred aromatic groups.

Hydrocarbon radicals from which $R_2$ is selected can contain from 1 to 30 carbon atoms and may be aliphatic, cycloaliphatic, aromatic or a combination of such moieties. When $R_2$ is an alkyl group, i.e. an aliphatic hydrocarbon radical, it will contain from 1 to 30 and, more preferably, 1 to 20 carbon atoms and may be straight-chain or branched, saturated or unsaturated. Radicals which contain unsaturation generally have no more than one double bond for every four carbon atoms. Cycloaliphatic hydrocarbon radicals from which $R_2$ may be selected are saturated or unsaturated and can contain one or more hydrocarbon substituents on the ring. The cycloaliphatic radicals will have from 3 to 30 carbon atoms, however, preferred cycloaliphatic radicals contain from 5 to 20 carbon atoms and correspond to the formula

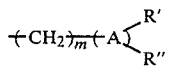

where m is an integer from 0 to 8 and, more preferably, 0 to 4, A represents a non-aromatic 5- or 6-membered carbon ring system, and R′ and R″ are hydrogen, a $C_{1-8}$ alkyl or alkenyl group, phenyl or benzyl. Particularly advantageous cycloaliphatic radicals of the above type are those wherein the moiety

is an unsubstituted or mono- $C_{1-8}$ alkyl- or alkenyl-substituted cyclopentyl, cyclopentenyl, cyclohexyl, cyclohexenyl or cyclohexa-2,4-dienyl group. When $R_2$ is an aromatic hydrocarbon radical, it will contain from 6 to about 30 carbon atoms and may consist of a single ring or fused-ring system which can be unsubstituted or have one or more hydrocarbon groups substituted thereon. Especially useful aromatic radicals contain from 6 to 20 carbon atoms and correspond to the formula

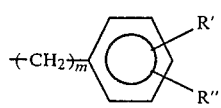

where m is an integer from 0 to 8, and more preferably 0 to 4, and R′ and R″ are hydrogen a $C_{1-8}$ alkyl or alkenyl group, phenyl or benzyl. Preferred aromatic radicals include phenyl, $C_{1-8}$ alkyl- or alkenyl-substituted phenyl, benzyl and $C_{1-8}$ alkyl- or alkenyl-substituted benzyl.

$R_2$ can also be an aliphatic, cycloaliphatic or aromatic moiety containing one or more oxygen, sulfur, nitrogen or halogen atoms, or a combination thereof. Such radicals can result from the substitution of a functional group on an aliphatic, cycloaliphatic or aromatic hydrocarbon radical, such as those previously described, or in the case of oxygen, sulfur and nitrogen, the atoms may be an integral part of a hydrocarbon chain or ring structure, i.e., $R_2$ is a heteroalkyl or heterocyclic radical. In the situation when the aliphatic, cycloaliphatic, or aromatic group is substituted with the functional group, the substituent may be halogen (fluorine, chlorine or bromine), nitro, amine, nitrile, thionitrile, isothionitrile, mercapto, hydroxy and the like. One or more of these groups may be substituted on the hydrocarbon chain or ring system which can contain up to 30 carbon atoms. $R_2$ can also be oxoalkyl or oxocycloalkyl radicals such as, for example

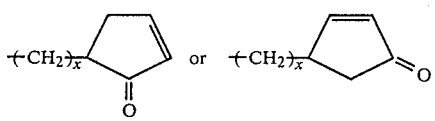

where x is 0 or 1 and the various ring positions may be substituted with a $C_{1-4}$ alkyl or alkenyl, phenyl, benzyl or phenoxy group.

When $R_2$ is a heteroalkyl or heterocyclic radical wherein the oxygen, sulfur or nitrogen forms an integral part of the hydrocarbon chain or hydrocarbon ring system, the radical will contain up to 30 carbon atoms. Especially useful heteroalkyl radicals contain from 2 to 20 carbon atoms and are derived from alkanolamines, such as ethanolamine; N,N-dialkylalkanolamines, such as N,N-dimethylethanolamine, and quaternized derivatives thereof; monoalkyl ethers of polyalkylene glycols, such as diethylene glycol, and higher poly(oxyalkylene)glycols; and the like. Especially useful heterocyclic radicals contain from 4 to 20 carbon atoms and have a 5- or 6-membered ring, or fused ring structure thereof. More than one heteroatom may be present in the ring and the heteroatoms need not be the same. Illustrative heterocyclic groups include:

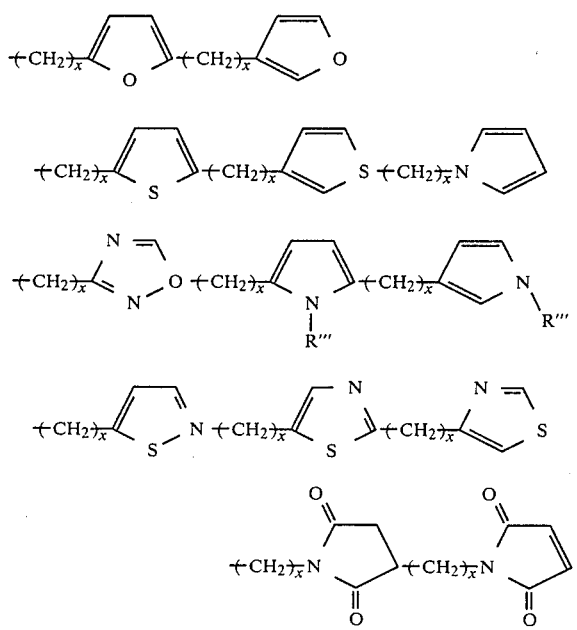

wherein x is 0 or 1, R''', is hydrogen or $C_{1-4}$ alkyl, and each of the available ring positions may be substituted with a $C_{1-4}$ alkyl or alkenyl, phenyl, benzyl or phenoxy group and wherein hydrocarbon groups on adjacent positions may be joined to form a ring.

Useful pesticidal and herbicidal 2-ethyl- and 2-vinyl-cyclopropane monocarboxylate compounds of this invention are obtained when $R_2$ is a heteroalkyl or heterocyclic radical. As employed herein, the term herbicide is used in its broadest sense to encompass any type of modification of plant growth including retardation of growth, defoliation, dessication, regulation, stimulation, dwarfing and, in some cases, killing the plant. In addition to treatment of established plants and emerging seedlings, the vinylcyclopropane monocarboxylate compounds of this invention can also be applied as a seed coating. The term insecticide is also used in the broad sense wherein it encompasses not only usage for the control of beetles, flies and mosquitos but also use for the control of spiders, lice, mites, ticks, nemotodes and other pests not classified as insects in the strict biological sense. Various isomeric forms will exhibit more activity than other isomers for certain of these applications. Particularly useful heteroalkyl or heterocyclic groups for this purpose have from 3 to 20 carbon atoms and are selected from:

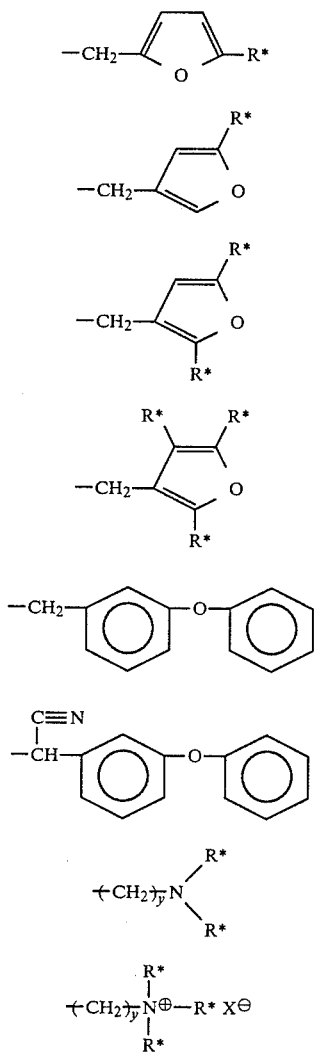

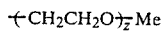

or

where R* is a $C_{1-4}$ alkyl, $C_{1-4}$ alkenyl, $C_{1-4}$ hydroxyalkyl, phenyl or benzyl, Me is methyl, Et is ethyl, y is an integer from 2 to 6, z is an integer from 1 to 10 and X represents an anion such as halide, hydroxide, sulfate, nitrate, acetate, alkylsulfate, alkylphosphate, fluoroborate and the like.

Especially useful products of this invention, by virtue of the fact that they can be readily prepared and are useful as such as fragrance compounds and as chemical intermediates, are the lower alkyl cyclopropane monocarboxylates wherein $R_1$ is an alkyl or alkenyl group having from 4 to 8 carbon atoms, phenyl, benzyl or $C_{1-4}$ alkyl- or $C_{1-4}$ alkoxy-substituted phenyl or benzyl and $R_2$ is a $C_{1-4}$ alkyl group. These compounds are conveniently prepared utilizing the phase transfer process of U.S. Pat. No. 4,252,739, details of which are incorporated herein by reference. This process involves reacting an alkylating agent and an activated methylene compound in the presence of an onium compound, an alkali metal compound and water. To obtain the preferred lower alkyl cyclopropane monocarboxylate compounds by the process of U.S. Pat. No. 4,252,739, a $C_{1-4}$ alkyl ester of an α-keto substituted acetic acid is reacted with an alkylating agent, typically a 1,4-dihalobutene-2. The reaction is represented by the equation:

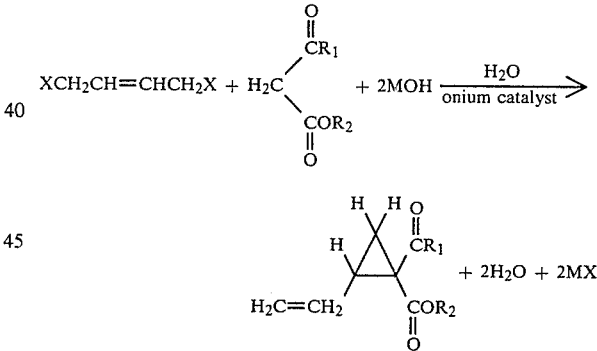

where X represents a halogen atom, M represents an alkali metal, $R_1$ is a $C_{4-8}$ alkyl or alkenyl, phenyl, benzyl or $C_{1-4}$ alkyl- or $C_{1-4}$ alkoxyl-substituted phenyl or benzyl and $R_2$ is a $C_{1-4}$ alkyl group. For example, in the case where ethyl acetoacetate ($R_1$=methyl; $R_2$=ethyl) is reacted in accord with the above equation, ethyl 2-vinyl-1-acetocyclopropane-1-carboxylate is obtained. To obtain the corresponding ethyl 2-ethyl-1-acetocyclopropane-1-carboxylate a reduction of the vinyl group would be carried out. The reduction method of choice will be any procedure which will not reduce the keto function or cause opening of the cyclopropane ring.

The lower alkyl cyclopropane monocarboxylates so obtained are useful as fragrance chemicals and as fragrance intermediates, however, they may also be utilized for the preparation of the more complex cyclopropane carboxylates of this invention, i.e., vinylcyclopropane compounds wherein the ester moiety is a bulky hydrocarbon group, a heteroalkyl or heterocyclic group, or contains one or more functional groups. For example, the lower alkyl cyclopropane monocarboxylates obtained by the process of U.S. Pat. No. 4,252,739 can be hydrolyzed to obtain the acid and the resulting cyclopropane monocarboxylic acid esterified with an alcohol or alcohol mixture employing conventional esterification procedures. Additionally, the cyclopropane monocarboxylic acid can be converted to the alkali metal salt and reacted with a suitable active halide compound or the cyclopropane monocarboxylic acid can be converted to the acid halide and reacted with the alcohol or corresponding metal alkoxide. More commonly, however, the lower alkyl esters are utilized as such and subjected to a transalcoholysis reaction with the desired alcohol. Transalcoholysis of the lower alkyl cyclopropane monocarboxylates can be readily carried out in accordance with known procedures and utilizing a wide variety of alcohols or mixtures of alcohols to obtain 2-vinyl(or ethyl)-1-ketocyclopropane-1-carboxylates having widely diverse ester moieties.

Illustrative alcohols, or halides or alkoxides derived from these alcohols, which can be used to obtain the products of this invention in accordance with the above-mentioned procedures include but are not limited to the following:

2-methyl-1-pentanol
2-ethylhexanol
2-octanol
2,6-dimethyl-4-heptanol
dodecanol
hexadecanol
octadecanol
allyl alcohol
3-methyl-1-buten-3-ol
3-ethyl-1-buten-3-ol
3-methyl-3-penten-1-ol
1,4-pentadien-3-ol
5-cyclohexylidene-2-pentanol
2-methyl-2-hepten-6-ol
5,6-dimethyl-5-hepten-2-ol
6,10-dimethylundeca-5,9-dien-2-ol
3,7,11-trimethyldodeca-1,6,10-trien-3-ol
cyclopentanol
cyclohexanol
4-methylcyclohexanol
3-cyclobutyl-2-propen-1-ol
3-cyclopentyl-2-propen-1-ol
3-cyclohexyl-2-propen-1-ol
3-cycloheptyl-2-propen-1-ol
3-(4-chlorophenyl)-3-methyl-2-propen-1-ol
3-(4-methylphenyl)-3-methyl-2-propen-1-ol
3-(4-methylphenyl)-2-butyl-2-propen-1-ol
3-(4-methoxyphenyl)-1-methyl-2-propen-1-ol
3-(1-naphthyl)-2-propen-1-ol
3-(4-chloronaphth-1-yl)-2-propen-1-ol
3-(4-methylnaphth-1-yl)-2-propen-1-ol
benzyl alcohol
(3-phenoxyphenyl)carbinol
(3-thiophenyl)carbinol
2,4-dimethylbenzyl alcohol
2,4,6-trimethylbenzyl alcohol
4-allylbenzyl alcohol
2,6-dimethyl-4-allylbenzyl alcohol
4-(3'-methylbenzyl)benzyl alcohol
4-(2',4'-dimethylbenzyl)benzyl alcohol
2,6-dichlorobenzyl alcohol
benzhydrol
cinnamyl alcohol
p-methoxycinnamyl alcohol
2,4,5-trimethoxycinnamyl alcohol
p-benzylcinnamyl alcohol
p-benzyloxycinnamyl alcohol
m-bromocinnamyl alcohol
3-chloro-4-methoxycinnamyl alcohol
o-methoxycinnamyl alcohol
p-isopropoxycinnamyl alcohol
p-phenoxycinnamyl alcohol
p-methylcinnamyl alcohol
p-(methylphenethyl)cinnamyl alcohol
phenol
cresol
eugenol
isoeugenol
thymol
α-hydroxyacetophenone
cyclohexylphenol
t-butylphenol
nonylphenol
naphthol
2-phenoxyethanol
diethylene glycol monomethyl ether
triethylene glycol monoethyl ether
monoethanol amine
diethanol amine
triethanol amine
N-aminoethylethanol amine
2-(2-aminoethoxy)ethanol
3-Bis(2-hydroxyethyl)aminopropylamine
N-hydroxyethylethylene diamine
N-methyldiethanol amine
2-(2-(3-aminopropoxy)ethoxy)ethanol
2-methylaminoethanol
2-dimethylaminoethanol
2-diethylaminoethanol
N-2-hydroxyethylacetamide
2-anilinoethanol
2-N-ethylanilinoethanol
1-dimethylamino-2-propanol
1-(2-aminoethylamino)-2-propanol
4-(2'-thenyl)benzyl alcohol
furfuryl alcohol
(3-furyl)carbinol
thiofurfuryl alcohol
4-(2'-furfuryl)benzyl alcohol
(5-benzyl-3-furyl)carbinol
2-(2',4'-dimethylbenzyl)-4-furfuryl alcohol
(5-benzyl-2-furyl)carbinol
(4-benzyl-5-methyl-2-furyl)carbinol
2-(4'-methylbenzyl)-5-furfuryl alcohol
(3-methyl-2-furyl)carbinol
(2-methyl-3-furyl)carbinol
(5-methyl-3-furyl)carbinol
(5-methyl-2-furyl)carbinol
(2,5-dimethyl-3-furyl)carbinol
(2,4,5-trimethyl-3-furyl)carbinol
(5-allyl-2-furyl)carbinol
(5-allyl-3-furyl)carbinol
5-hydroxymethyl-2,2'-difurylmethane
4-hydroxymethyl-2,2'-difurylmethane
4-hydroxymethyl-2,2'-difurylmethane
(4,5-benzo-2-furyl)carbinol
(4,5-benzo-3-furyl)carbinol
5-phenoxy-2-thienyl alcohol
N-hydroxymethyl-3,4,5,6-tetrahydrophthalimide N-hydroxymethyl phthalimide
N-hydroxymethyl thiophthalimide
N-hydroxymethyl-3,6-dihydrophthalimide
N-hydroxymethyl dimethylmaleimide
N-hydroxymethyl methylethylmaleimide
N-hydroxymethyl phenylmethylmaleimide
3-hydroxymethyl-5-benzyl-1,2,4-oxadiazole
1-benz-4-hydroxymethylpyrazole
3-methyl-2-cyclopenten-4-ol-1-one
2-allyl-3-methyl-2-cyclopenten-4-ol-1-one.

The 2-vinyl-1-alkanoylcyclopropane-1-carboxylates of this invention are similar in structure to the well known pyrethrin natural products which occur in essential oils of certain flowers. As such, they have odors that would be useful in recreating floral compositions.

The following examples more fully illustrate the preparation of the novel cyclopropane monocarboxylate compounds of this invention and intermediates thereof. The examples are not intended to limit the scope of the invention and numerous variations are possible as will be evident to those skilled in the art to which the invention pertains.

EXAMPLE I

Ethyl 2-vinyl-1-hexanoylcyclopropane-1-carboxylate was obtained by the phase transfer reaction of ethyl hexanoylacetate and 1,4-dichlorobutene-2. To prepare the ethyl hexanonylacetate, 4 moles diethyl carbonate was slowly added to 4 moles sodium hydride dispersed in anhydrous ethyl ether with stirring and under a nitrogen atmosphere. When the addition was complete, the mixture was heated to reflux and 2 moles of 2-heptanone (in 200 ml ethyl ether) added dropwise. The rate of addition was controlled to maintain steady reflux. At the completion of reaction 269 ml (4.7 moles) glacial acetic acid was added with stirring and 1200 ml water added to dissolve the sodium acetate formed. After separation of the organic and aqueous layers, the organic layer was dried over magnesium sulfate and ether evaporated under vacuum. The resulting crude product was vacuum distilled to provide 91% yield ethyl hexanonylacetate (B.p. 109°–112° C. at mm Hg.).

The ethyl hexanonylacetate (80 gms; 0.43 mole) was combined with 1,4-dichlorobutene-2 (67.3 gms.; 0.54 mole) and this mixture added dropwise with stirring at room temperature to a mixture of potassium hydroxide (0.86 mole) and 5 mole percent tricaprylylmethylammoinum chloride in methylene chloride.

The temperature during the dropwise addition was maintained at 25° C. with external cooling. When the addition was complete and after stirring for 3 additional hours at 25° C., water was added to the reaction mixture to dissolve the suspended salts. The organic portion was recovered, dried over magnesium sulfate, and after removal of a portion of the methylene chloride, passed through a silica column. The remainder of the methylene chloride was then removed to obtain crude ethyl 2-vinyl-1-hexanoylcyclopropane-1-carboxylate in 88% yield. Vacuum distillation of the crude material yielded 95% pure ethyl 2-vinyl-1-hexanoylcyclopropane-1-carboxylate (B.p. 74°–75° C. at 0.01 mm Hg; $n_D^{25}$ 1.4607). The structure of the product was confirmed by mass spectroscopy and nuclear magnetic resonance spectroscopy.

Mass spectrum m/e: 238(M+).

nmr (CDCl$_3$)$\tau$ 4.35–4.90 (3 vinyl H, mult.); 5.65(2H, q); 6.90–7.60 (1H(2-ring position), 2H(—COCH$_2$—), br. mult.); 8.00–8.45 (2H(3-ring position), mult.); 8.45–8.85 (6H(—CH$_2$CH$_2$CH$_2$—), mult.); 8.67 (3H, tr.); 9.07(3H, tr.).

The product had an intense live green floral odor and is a useful fragrance intermediate. Also, effective insecticidal compounds are obtainable from the ethyl 2-vinyl-1-hexanoylcyclopropane-1-carboxylate by transalcoholysis with m-phenoxybenzyl alcohol or (5-benzyl-3-furyl)carbinol.

EXAMPLE II

In a manner similar to that described in Example I ethyl 4-methylpentanoylacetate (B.p. 85°–88° C. at 4 mm Hg) was prepared. The ethyl 4-methylpentanoylacetate (0.54 mole) was reacted with 1,4-dichlorobutene-2 (0.68 mole) and potassium hydroxide (1.08 moles) in 400 ml methylene chloride and in the presence of 5 mole percent tricaprylylmethylammonium chloride. After maintaining the reaction mixture at 25°–35° C. for 2 hours, suspended solids were removed by filtration and the organic layer worked up to recover the crude ethyl 2-vinyl-1-(4-methylpentanoyl)cyclopropane-1-carboxylate, which had a pleasant fruity odor, and was confirmed by infrared, mass spectroscopy and nuclear magnetic resnance spectroscopy.

Mass spectrum m/e 238 (M+).

nmr (CDCl$_3$)$\tau$ 4.30–4.95 (3 vinyl H, mult.); 5.65 (2H, q); 6.74–7.57 (1H(2-ring position); 2H(—COCH$_2$—), br. mult.); 7.98–8.65 (2H(3-ring position), 5H(—CH$_2$CH$_2$-CH<), mult.); 8.65 (3H, tr.); 8.81–9.20 (6H, mult.).

EXAMPLE III

In a similar manner, ethyl 5-methyl-4-hexenonylacetate was prepared (B.p. 89°–90° C. at 1 mm Hg) and 0.21 mole of this product reacted with 0.25 mole 1,4-dichlorobutene-2 and 0.42 mole potassium hydroxide in the presence of 5 mole percent quaternary ammonium catalyst. After workup of the reaction mixture, 53.5 gms. crude product was recovered. Gas chromatographic analysis indicated that the crude material contained approximately 75% of the desired ethyl 2-vinyl-1-(5-methyl-4-hexenonyl)cyclopropane-1-carboxylate product. A portion of the crude product was vacuum distilled, and infrared and nuclear magnetic resonance spectroscopic analysis of the distilled ethyl 2-vinyl-1-(5-methyl-4-hexenoyl)cyclopropane-1-carboxylate confirmed the structure.

EXAMPLE IV

Ethyl benzoylacetate (0.24 mole) obtained from a commercial supplier was reacted with 0.3 mole 1,4-dichlorobutene-2 and 0.48 mole potassium hydroxide in accordance with the procedure of Example I, except that acetonitrile was employed as the reaction medium. At the completion of the reaction, the reaction mixture was poured into a 1200 cc water, vigorously shaken and extracted (five times) with petroleum solvent, the combined organic extracts, after drying, were evaporated under vacuum to yield 30.7 gms. crude product containing 59% ethyl 2-vinyl-1-benzoylcyclopropane-1-carboxylate. A purified sample of the ethyl 2-vinyl-1-benzoylcyclopropane-1-carboxylate (B.p. 80° C. at 0.25 mm Hg) had a pleasing odor suitable for fragrance uses.

nmr (CDCl$_3$)$\tau$ 1.75–2.60 (6 phenyl H, mult.); 4.13–5.02 (3 vinyl H, mult.); 5.85 (2H(—CO$_2$CH$_2$—, cis/trans), d.q.); 7.05 (1H(2-ring position), br. mult.); 7.90–8.65 (2H(3-ring position), mult.); 9.05 (3H(cis/trans); d.tr.).

We claim:

1. A process for augmenting or enhancing the aroma of a fragrance formulation comprising the step of adding to said formulation an aroma augmenting or enhancing quantity of a vinylcyclopropane compound of the structure

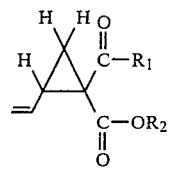

where $R_1$ is an alkyl or alkenyl group having 4 to 8 carbon atoms and $R_2$ is a $C_{1-4}$ alkyl group.

2. The process of claim 1 wherein the vinylcyclopropane compound is ethyl 2-vinyl-1-hexanoylcyclopropane-1-carboxylate.

3. The process of claim 1 wherein the vinylcyclopropane compound is ethyl 2-vinyl-1-(4-methylpentanoyl)-cyclopropane-1-carboxylate.

4. The process of claim 1 wherein the vinylcyclopropane compound is ethyl 2-vinyl-1-(5-methyl-4-hexenoyl)cyclopropane-1-carboxylate.

* * * * *